(12) United States Patent
Kumamoto et al.

(10) Patent No.: US 6,838,106 B2
(45) Date of Patent: Jan. 4, 2005

(54) WARMING COMPOSITION FOR FOOD AND DRINK OR FOR ORAL CARE PREPARATION

(75) Inventors: Hiroyasu Kumamoto, Tokyo (JP); Tatsuo Kitamura, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 188 days.

(21) Appl. No.: 10/006,137

(22) Filed: Dec. 10, 2001

(65) Prior Publication Data

US 2002/0119231 A1 Aug. 29, 2002

(30) Foreign Application Priority Data

Dec. 12, 2000 (JP) ........................... P. 2000-376814

(51) Int. Cl.⁷ ........................... A23L 2/56; A61K 31/11
(52) U.S. Cl. .................. 426/536; 426/534; 426/538; 426/650; 514/699
(58) Field of Search ................. 426/534, 536, 426/538, 650; 514/699

(56) References Cited

U.S. PATENT DOCUMENTS

| | | |
|---|---|---|
| 4,866,210 A | 9/1989 | Helderich et al. |
| 5,545,424 A | 8/1996 | Nakatsu et al. |
| 5,628,986 A | 5/1997 | Sanker et al. |
| 5,753,609 A | 5/1998 | Nakatsu et al. |
| 6,306,429 B1 | 10/2001 | Bealin-Kelly |
| 6,673,844 B2 * | 1/2004 | Kumamoto et al. ........ 514/699 |

FOREIGN PATENT DOCUMENTS

| | | |
|---|---|---|
| EP | 0988852 A2 | 3/2000 |
| EP | 1 121 927 A2 | 8/2001 |
| GB | 762421 A | 11/1956 |
| GB | 824 680 A | 12/1959 |
| JP | 2000-26268 | 1/2000 |
| WO | WO 97/02273 | 1/1997 |
| WO | 97/02273 * | 1/1997 |
| WO | WO 98/47483 | 11/1998 |

* cited by examiner

*Primary Examiner*—Leslie Wong
(74) *Attorney, Agent, or Firm*—Sughrue Mion, PLLC

(57) ABSTRACT

This invention relates to a warming composition for food and drink or for oral care preparations which produces an excellent and long-lasting warming effect and causes no or little irritation to mucous membranes, a flavor composition for food and drink or for oral care preparations which comprises the warming composition, and beverages or oral care preparations which contain the warming composition or the flavor composition.

9 Claims, No Drawings

WARMING COMPOSITION FOR FOOD AND DRINK OR FOR ORAL CARE PREPARATION

FIELD OF THE INVENTION

This invention relates to a warming composition for food and drink or for oral care preparations which produces an excellent and long-lasting warming effect and causes no or little irritation to mucous membranes, a flavor composition for food and drink or for oral care preparations which comprises the warming composition, and beverages or oral care preparations which contain the warming composition or the flavor composition.

BACKGROUND OF THE INVENTION

Substances which are known to provide a sensation of warmth on application and called "warming agents" include polyhydric alcohols, capsicum (red pepper) powder, a capsicum tincture, capsicum extract, capsaicin, homocapsaicin, homodihydrocapsaicin, nonanoyl vanillyl amide, nonanoic acid vanillyl ether, vanillyl alcohol alkyl ether derivatives (JP-A-57-9729), such as vanillyl ethyl ether, vanillyl butyl ether, vanillyl pentyl ether, and vanillyl hexyl ether, isovanillyl alcohol alkyl ethers, ethylvanillyl alcohol alkyl ethers, veratryl alcohol derivatives, substituted benzyl alcohol derivatives, substituted benzyl alcohol alkyl ethers, vanillin propylene glycol acetal, ethylvanillin propylene glycol acetal, ginger extract, ginger oil, gingeol, and gingeron.

The warming composition is added either directly as such or in the form of a flavor composition to beverages and oral care preparations to produce a warming effect. However, the known warming agents often cause strong irritation on mucous membranes or exhibit insufficient warming effects, and those having high warming effects are of short duration or, when used in a reduced amount, have insufficient warming effects or an insufficient duration of effect.

An object of the present invention is to provide a warming composition for food and drink and for oral care preparations which is freed of these problems, i.e., causes no or little mucous membrane irritation and exhibits an excellent and long-lasting warming effect in a small amount.

Another object of the present invention is to provide a flavor composition which causes no or little mucous membrane irritation and imparts a long-lasting warming effect when added in a small amount.

Still another object of the invention is to provide foods, beverages, and oral care preparations which contain the warming composition or the flavor composition and exhibit excellent and long-acting warming effects.

As a result of extensive investigations, the inventors have found that a combination of a compound or a composition that has been known as a cooling agent (hereinafter inclusively referred to as a cooling agent) and a small amount of a compound represented by formula (I)(B) and/or a compound or a composition that has been known as a warming agent (hereinafter inclusively referred to as a warming agent) produces such a warming effect as is never expected from each of the components used alone and as lasts as long as 3 hours or even more, and, when added to a product, exhibits an appreciable warming effect in such a low concentration at which each component would not stimulate individually, making it possible to produce a warming effect with no skin irritation that has not heretofore been attained.

The present invention provides a warming composition for food and drink and for oral care preparations comprising (A) a cooling agent and (B) a compound represented by formula (I):

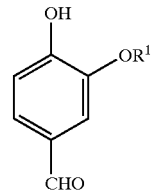

wherein $R^1$ represents a hydrogen atom, a methyl group or an ethyl group.

The present invention also provides a warming composition for food and drink and for oral care preparations comprising (A) a cooling agent and (C) a warming agent.

The present invention also provides a warming composition for food and drink and for oral care preparations comprising (A) a cooling agent, (B) a compound represented by formula (I), and (C) a warming agent.

The present invention also provides a flavor composition for beverage and food or an oral care preparation comprising any of the above-described warming compositions.

The present invention also provides a food, a beverage or an oral care preparation comprising any of the above-described warming compositions or the above-described flavor composition.

In the present invention, a combination of a cooling agent and at least one of a warming agent and a specific compound produces an appreciable warming effect at such a low concentration at which each component alone is ineffective. The warming effect of the warming composition of the invention lasts for a long period of time that has not been thought. The warming composition of the invention is unlike conventional ones in that when it is applied to one's sole, the warming effect is also produced in her or his back, etc.

The warming composition of the present invention comprises (A) a cooling agent and at least one of (B) a compound represented by formula (I) and (C) a warming agent.

The cooling agent as component (A) can be any compound or composition known as a cooling agent. Typical examples of the cooling agents which can be used in the invention include:

(1) a compound represented by formula (II):

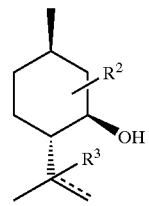

wherein $R^2$ and $R^3$ each represent a hydrogen atom or a hydroxyl group (=== represents a single bond or a double bond, the same definition applies hereinafter), (2) a compound represented by formula (III):

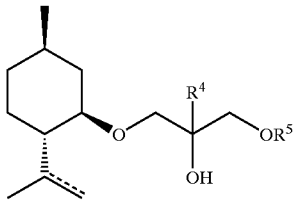

(III)

wherein $R^4$ represents a hydrogen atom or a methyl group; $R^5$ represents a hydrogen atom, a lower alkyl group or a 2-alkoxyethyl group, (3) a compound represented by formula (IV):

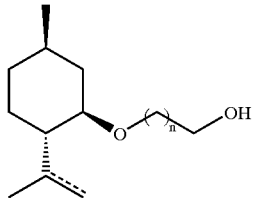

(IV)

wherein n represents an integer of 1 to 10, (4) a compound represented by formula (V):

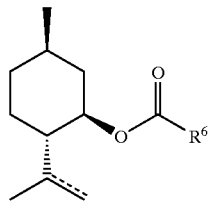

(V)

wherein $R^6$ represents a hydrogen atom, a straight-chain or branched alkyl or alkenyl group, or a straight-chain or branched hydroxyalkyl group, (5) l-menthylacetic acid N-ethylamide, and (6) N,2,3-trimethyl-2-(1-methylethyl)-butanamide.

Specific examples of the cooling agents which are preferably used in the invention include, but are not limited to, menthol, isopulegol, 3-(l-menthoxy)propane-1,2-diol, 3-(l-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, Japanese mint (Mentha arvensis) oil, peppermint oil, menthone, menthone glycerol ketal, menthyl lactate, 3-(l-menthoxy)ethan-1-ol, 3-(l-menthoxy)propan-1-ol, 3-(l-menthoxy)butan-1-ol, l-menthylacetic acid N-ethylamide, l-menthyl-4-hydroxypentanoate, l-menthyl-3-hydroxybutyrate, N,2,3-trimethyl-2-(1-methylethyl)-butanamide, and spearmint oil.

Of these cooling agents preferred are 3-(l-menthoxy)propane-1,2-diol, 3-(l-menthoxy)-2-methylpropane-1,2-diol, p-menthane-3,8-diol, 3-(l-menthoxy)ethan-1-ol, 3-(l-menthoxy)propan-1-ol, and 3-(l-menthoxy)butan-1-ol. Still preferred are 3-(l-menthoxy)propane-1,2-diol and 3-(l-menthoxy)-2-methylpropane-1,2-diol.

Of the compounds represented by formula (I) as component (B) the compound in which $R^1$ is a methyl group, i.e., vanillin is preferred.

The warming agent as component (C) includes, but is not limited to, (i) vanillyl alcohol, vanillyl alkyl or alkenyl ethers represented by formula (VI):

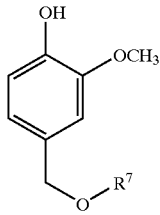

(VI)

wherein $R^7$ represents a hydrogen atom or a straight chain or branched alkyl or alkenyl group having 1 to 10 carbon atoms, preferably 1 to 6 carbon atoms, such as vanillyl ethyl ether, vanillyl propyl ether, vanillyl butyl ether, vanillyl pentyl ether, and vanillyl hexyl ether;

(ii) vanillin propylene glycol acetal;

(iii) ethylvanillin propylene glycol acetal;

(iv) compounds represented by formula (VII):

(VII)

wherein $R^8$ represents a straight-chain or branched alkyl or alkenyl group, (v) gingeron, 4-(1-menthoxymethyl)-2-(3',4'-dihydroxyphenyl)-1,3-dioxolane, 4-(1-menthoxymethyl)-2-(2'-hydroxy-3'-methoxyphenyl)-1,3-dioxolan, capsicum tincture, and ginger extract. Any other substances that have been used as a warming agent, including those described in the background of the present invention, can be used.

Of the above recited warming agents preferred are vanillyl ethyl ether, vanillyl propyl ether, vanillyl butyl ether, vanillyl pentyl ether, vanillyl hexyl ether, gingeron, capsicum tincture, and ginger extract. Still preferred are vanillyl butyl ether, vanillyl pentyl ether, vanillyl hexyl ether, and capsicum tincture. Vanillyl butyl ether is the most preferred.

Component (B) is usually used in an amount of 0.000001 to 100 parts, preferably 0.0001 to 10 parts, still preferably 0.001 to 1 part, by weight per part by weight of component (A), and component (C) is usually used in an amount of 0.5 to 100 parts, preferably 0.5 to 10 parts, still preferably 0.5 to 1 part, by weight per part by weight of component (A). Where the warming composition comprises both components (B) and (C), components (B) and (C) are used in an a total amount of 0.000001 to 100 parts, preferably 0.0001 to 10 parts, by weight per part by weight of component (A). The weight ratio of component (C) to component (B) is preferably 0.01 to 100.

A preferred combination of components (A), (B), and (C) includes a combination of (A) 3-(l-menthoxy)propane-1,2-diol or 3-(l-menthoxy)-2-methylpropane-1,2-diol and (B) vanillin and/or (C) vanillyl butyl ether. In this case, the combination usually comprises 0.0001 to 10 parts by weight, preferably 0.01 to 10 parts by weight, of component (B) and 0.5 to 5 parts by weight of component (C) each per part by weight of component (A).

The warming composition for food and drink or for oral care preparations, which comprises component (A) and components (B) and/or (C), may be diluted with a diluent safe to a human body, such as ethanol or pure water at an appropriate dilution decided according to the intended use, for example, about 1:2 to 1:10000.

The warming composition can be incorporated into a flavor composition for food and drink or oral care preparations. The flavor composition which can be used is not particularly limited, and any flavorings known in the art for use in foods, beverages or oral care products can be used. Examples of suitable flavorings include citrus flavors, such as an orange flavor, a lemon flavor, a lime flavor, a grapefruit flavor, a yuzu (Chinese lemon) flavor, and a sudachi flavor; fruit flavors, such as an apple flavor, a grape flavor, a strawberry flavor, a pineapple flavor, a banana flavor, a peach flavor, a melon flavor, an apricot flavor, an ume (Japanese apricot) flavor, a cherry flavor, a raspberry flavor, a blueberry flavor, and a tropical fruit flavor; milk flavors, such as a milk flavor, a butter flavor, a cheese flavor, a cream flavor, and a yogurt flavor; a vanilla flavor; tea or coffee flavors, such as a green tea flavor, a oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a camomile flavor, a mustard flavor, a cardamon flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a capsicum flavor, a nutmeg flavor, a basil flavor, a marjoram flavor, a rosemary flavor, a bayleaf flavor, and a wasabi (Japanese horseradish) flavor; meat flavors, such as a beef flavor, a pork flavor, and a chicken flavor; marine flavors, such as a fish flavor, a shell flavor, a crustacean flavor, a dried and smoked fishes flavor, and a seaweed flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor. For the details of compositions of these flavors, refer to Japanese Patent Office Gazette 12(2000)-1[7270], Known and Customary Techniques (Perfumes), II. Food Flavors. The warming composition of the invention can be used as a blending component or an additive component in flavor blending or as an additive after blending.

The warming composition or the flavor composition of the invention for food and drink and for oral care preparations can be used as an additive component to various products. The content of the warming composition in a final product is subject to wide variation according to the kind of the product, the amount of the product to be applied, the mode of use or application of the product, and the like. In general, the content of each of components (A), (B), and (C) in a final product can range from 0.000001 to 10%, preferably 0.0001 to 1%, still preferably 0.001 to 0.5%, by weight based on the final product. Component (A) and components (B) and/or (C) may be added to a product either separately with or without an appropriate solvent or in the form of a composition previously prepared from the components (i.e., the warming composition or the fragrance composition). They may be added as compounding components in the course of producing the product.

The warming composition for food and drink or for oral care preparations of the present invention can be used in flavor preparations, food and drink, or oral care preparations as a component for providing sensation of warmth or a component for prolonging sensation of warmth. The products to which the warming composition of the invention is applicable include, but are not limited to, food and drink, such as candies, drops, chewing gums, tablets, chocolates, cakes, cookies, snack food, bread, tea, coffee, juice, fruit drinks, fruit wine, dairy drinks, carbonated beverages, alcoholic beverages, seasonings, salad dressings, and dips; and oral care preparations, such as mouthwash, toothpaste, nebulizers, drinks, medicinal drops, gargles, and chewables.

In addition to the warming composition of the invention, these products can contain other additives according to use. For example, additives permitted by Food Sanitation Law can be added to food and drink according to necessity. Useful additives include saccharides, sweeteners, inorganic salts, emulsifiers, acidifiers, flavorings, colors, antioxidants, raising agents, thickeners, vegetable oils, milk, and other dairy products. In some detail, bakery products can comprise wheat flour (base), butter, a raising agent, e.g., baking powder, an emulsifier, e.g., a sucrose fatty acid ester, saccharides, e.g., sugar, inorganic salts, and flavorings. Chocolate can comprise cacao mass (base) cacao butter, saccharides, e.g., sugar, milk, and an emulsifier. Emulsified dressings can comprise salad oil, water, vinegar, sugar, thickening polysaccharides, and sweeteners. Chewing gum can comprise a gum base, saccharides, such as sugar, glucose and starch syrup, and flavors. Candy can comprise saccharides, acidifiers, e.g., citric acid, sweeteners, flavorings, and colors. Orange fruit drinks can comprise orange juice, sweeteners, e.g., isomerized sugars, acidifiers, e.g., citric acid, and antioxidants, e.g., vitamin C. Fruit milk drinks can comprise fruit juice, dairy products such as milk and powdered skim milk, sacchardies, e.g., sugar, stabilizers, e.g., carboxymethyl cellulose, acidifiers, e.g., citric acid, and flavorings, e.g., a pineapple flavor.

Additives which can be used in the oral care preparations include inorganic salts, inorganic oxides, organic salts, thickeners, wetting agents, emulsifiers, surface active agents, humectants, alcohols, color additives, flavorings, and, if desired, medical ingredients such as crude drugs, hemostatics, circulation stimulants, antiinflammatory agents, astringents, antibacterial and/or antifungal agents, and bactericides. For example, toothpaste can comprise abrasives, such calcium phosphate, as calcium carbonate, aluminum hydroxide, silica, and calcium pyrophosphate; wetting agents, such as glycerin, sorbitol, and propylene glycol; tackifiers, such as carboxymethyl cellulose, carrageenan, and hydroxyethyl cellulose; surface active agents, such as sodium laurylsulfate, N-acylglutaminates, and sucrose fatty acid esters; sweeteners, such as saccharin sodium, stevioside, and xylitol; and medicinal components, such as vitamin E, azulene, aluminum chlorohydroxy allanthoinate, dextranase, hinokitiol, lysozyme chloride, and chlorhexidine.

The present invention will now be illustrated in greater detail with reference to Examples in view of Comparative Examples, but it should be understood that the invention is not limited thereto. Unless otherwise noted, all the percents are by weight.

Abbreviations used hereunder have the following meanings.
CA-10: 3-(l-Menthoxy)propane-1,2-diol
TPG-1: 3-(l-Menthoxy)-2-methylpropane-1,2-diol
TK-5: 3-(1-Methoxy)ethan-1-ol
VBE: Vanillyl butyl ether Particulars of commercially available products used hereunder are as follows. NIKKOL HCO-60: Polyoxyethylene hydrogenated castor oil (60E.O.), available from Nikko Chemicals Co., Ltd.

EXAMPLES 1 TO 4 AND COMPARATIVE EXAMPLES 1 TO 4

Warming Effect in Hard Candy

A panel consisting of three healthy males and four healthy females ate a piece of hard candy weighing 3 g having the formulation shown in Table 1 below and evaluated the warming effect and the irritation. The results of evaluation are shown in Table 1.

began to provide a tingling sensation attributed to VBE in the mouth during eating, which connected to long-lasting warmth felt deep in the throat.

EXAMPLES 5 TO 7 AND COMPARATIVE EXAMPLES 5 TO 8

Warming Effect in Chewing Gum

A panel consisting of three healthy males and four healthy females chewed gum weighing 3 g having the formulation shown in Table 2 below for 5 minutes and evaluated the warming effect and the irritation. The results of evaluation are shown in Table 2.

TABLE 1

| Formulation (%) | Example 1 | Example 2 | Example 3 | Example 4 | Compara. Example 1 | Compara. Example 2 | Compara. Example 3 | Compara. Example 4 |
| --- | --- | --- | --- | --- | --- | --- | --- | --- |
| Vanillin | 0.005 | 0.005 | — | 0.005 | — | — | 0.005 | — |
| VBE | — | — | 0.005 | 0.005 | — | — | — | 0.005 |
| CA-10 | 0.005 | — | 0.005 | 0.005 | 0.005 | — | — | — |
| TPG-1 | — | 0.005 | — | — | — | 0.005 | — | — |
| Granulated sugar | 52.3 | 52.3 | 52.3 | 52.3 | 52.3 | 52.3 | 52.3 | 52.3 |
| Starch syrup | 46.6 | 46.6 | 46.6 | 46.6 | 46.6 | 46.6 | 46.6 | 45.6 |
| Citric acid | 1 | 1 | 1 | 1 | 1 | 1 | 1 | 1 |
| Flavor | 0.09 | 0.09 | 0.09 | 0.085 | 0.095 | 0.095 | 0.095 | 0.095 |
| Effect |  |  |  |  |  |  |  |  |
| Sensation during eating | almost nothing felt | almost nothing felt | comfortable tingling | comfortable tingling | nothing felt | nothing felt | nothing felt | comfortable tingling |
| Sensation after 30 mins. | warmth in the throat | nice warmth in the throat | warmth in the throat | nice warmth in the throat | nothing felt | nothing felt | nothing felt | nothing felt |
| Sensation after 1 hr. | warmth in the throat | nice warmth in the throat | warmth in the throat | warmth in the throat | nothing felt | nothing felt | nothing felt | nothing felt |
| Irritation | comfortable irritation | no irritation | weak irritation | weak irritation | no irritation | no irritation | no irritation | weak irritation |

The candies of Comparative Examples 1 to 3 had no warming effect at all. The candy of Comparative Example 4 gave a tingling, which was attributed to VBE and comfortable to the mouth, which subsided gradually. The candies of Examples 1 to 4 produced the warming effect deep in the throat. Containing VBE, the candies of Examples 3 and 4

TABLE 2

| Formulation (%) | Example 5 | Example 6 | Example 7 | Compara. Example 5 | Compara. Example 6 | Compara. Example 7 | Compara. Example 8 |
| --- | --- | --- | --- | --- | --- | --- | --- |
| Vanillin | 0.005 | 0.005 | — | — | — | 0.005 | — |
| VBE | — | — | 0.005 | — | — | — | 0.005 |
| CA-10 | 0.005 | — | 0.005 | 0.005 | — | — | — |
| TPG-1 | — | 0.005 | — | — | 0.005 | — | — |
| Gum base | 21 | 21 | 21 | 21 | 21 | 21 | 21 |
| Powdered sugar | 66 | 66 | 66 | 66 | 66 | 66 | 66 |
| Starch syrup | 11.4 | 11.4 | 11.4 | 11.4 | 11.4 | 11.4 | 11.4 |
| Citric acid | 0.8 | 0.8 | 0.8 | 0.8 | 0.8 | 0.8 | 0.8 |
| Flavor | 0.79 | 0.79 | 0.79 | 0.795 | 0.795 | 0.795 | 0.795 |
| Effect |  |  |  |  |  |  |  |
| Sensation during chewing | almost nothing felt | almost nothing felt | comfortable tingling | nothing felt | nothing felt | nothing felt | comfortable tingling |
| Sensation after 30 mins. | warmth in the throat | nice warmth in the throat | warmth in the throat | nothing felt | nothing felt | nothing felt | nothing felt |
| Sensation after 1 hr. | warmth in the throat | nice warmth in the throat | warmth in the throat | nothing felt | nothing felt | nohting felt | nothing felt |

TABLE 2-continued

| Formulation (%) | Example 5 | Example 6 | Example 7 | Compara. Example 5 | Compara. Example 6 | Compara. Example 7 | Compara. Example 8 |
|---|---|---|---|---|---|---|---|
| Irritation | comfortable irritation | no irritation | weak irritation | no irritation | no irritation | no irritation | weak irritation |

The chewing gums of Comparative Examples 5 to 7 had no warming effect at all. The gum of Comparative Example 8 gave the mouth a comfortable tingling owing to VBE, which disappeared gradually. The gums of Examples 5 to 7 produced the warming effect deep in the throat. Containing VBE, the gum of Example 7 began to give a comfortable tingling attributed to VBE during chewing, which connected to a long-lasting sensation of warmth deep in the throat.

EXAMPLES 8 AND 9 AND COMPARATIVE EXAMPLES 9 TO 11

Warming Effect in Mouthwash

A panel consisting of three healthy males and four healthy females held 10 ml of mouthwash having the formulation shown in Table 3 below in their mouth for 10 seconds and then spat out to evaluate the warming effect and the irritation. The results of evaluation are shown in Table 3.

TABLE 3

| Formulation (%) | Example 8 | Example 9 | Compara. Example 9 | Compara. Example 10 | Compara. Example 11 |
|---|---|---|---|---|---|
| VBE | 0.005 | 0.005 | — | — | 0.005 |
| CA-10 | 0.005 | — | 0.005 | — | — |
| TPG-1 | — | 0.005 | — | 0.005 | — |
| 95% Ethanol | 5 | 5 | 5 | 5 | 5 |
| Nicol HCO-60 | 2 | 2 | 2 | 2 | 2 |
| Glycerin | 10 | 10 | 10 | 10 | 10 |
| Sodium benzoate | 0.05 | 0.05 | 0.05 | 0.05 | 0.05 |
| Purified water | 82.94 | 82.94 | 82.945 | 82.945 | 82.945 |
| Effect | | | | | |
| Sensation during washing | comfortable tingling | comfortable tingling | nothing felt | nothing felt | comfortable tingling |
| Sensation after 30 mins. | warmth in the throat | warmth in the throat | nothing felt | nothing felt | almost nothing felt |
| Sensation after 1 hr. | warmth in the throat | warmth in the throat | nothing felt | nothing felt | nothing felt |
| Irritation | comfortable irritation | comfortable irritation | no irritation | no irritation | comfortable irritation |

The mouthwashes of Comparative Examples 9 and 10 produced no warming effect at all. The mouthwash of Comparative Example 11 gave the mouth a comfortable tingling owing to VBE, which disappeared gradually. It was confirmed that the mouthwashes of Examples 8 and 9 give the mouth a comfortable tingling attributed to VBE, which connects to a long-lasting sensation of warmth deep in the throat.

The warming composition of the invention which comprises a cooling agent and a warming agent is incorporated into products to make the products exert an appreciable warming effect in such a low concentration at which each component would be ineffective when used individually. The warming composition makes it possible to produce a warming effect with no skin irritation that has not heretofore been attained. Further, the warming effect obtained by the present invention lasts long.

While the invention has been described in detail and with reference to specific embodiments thereof, it will be apparent to one skilled in the art that various changes and modifications can be made therein without departing from the spirit and scope thereof.

This application is based on Japanese patent application No. 2000-376814 filed Dec. 12, 2000, the entire contents thereof being hereby incorporated by reference.

What is claimed is:

1. A warming composition for food and drink and for oral care preparations which comprises a cooling agent and a compound represented by formula (I):

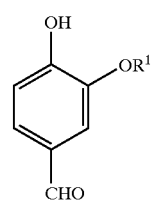

wherein $R^1$ represents a hydrogen atom, a methyl group or an ethyl group, and wherein the cooling agent is selected from the group consisting of menthol, isopulegol, 3-(l-menthoxy)-2-methylpropan-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, Japanese mint (Mentha arvensis) oil, peppermint oil, menthone, menthone glycerol ketal, menthyl lactate, 3-(l-menthoxy)ethan-1-ol, 3-(l-menthoxy)propan-1-ol, 3-(l-menthoxy)butan-1-ol, 1-menthyl-4-hydroxypentanoate, 1-menthyl-3-hydroxybutyrate, and spearmint oil.

2. A warming composition for food and drink and for oral care preparations which comprises a cooling agent and a warming agent, wherein the cooling agent is selected from the group consisting of menthol, isopulegol, 3-(l-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, Japanese mint (Mentha arvensis) oil, peppermint oil, menthone, menthone glycerol ketal, menthyl lactate, 3-(l-menthoxy)ethan-1-ol, 3-(l-menthoxy)propan-1-ol, 3-(l-menthoxy)butan-1-ol, 1-menthyl-4-hydroxypentanoate, 1-menthyl-3-hydroxybutyrate, and spearmint oil.

3. A warming composition for food and drink and for oral care preparations which comprises a cooling agent, a compound represented by formula (I):

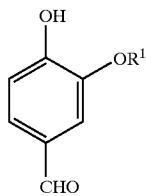

(I)

wherein $R^1$ represents a hydrogen atom, a methyl group or an ethyl group, and a warming agent.

4. A food, a beverage or an oral care preparation comprising the warming composition according to any one of claims 1 to 3.

5. A food, a beverage or an oral care preparation according to claim 4, wherein said cooling agent, said compound represented by formula (I)

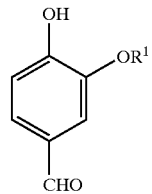

(I)

or said warming agent is present in an amount of 0.000001 to 10% by weight based on the weight of the total composition.

6. A flavor composition for food and drink or for oral care preparations which comprises the warming composition according to any one of claims 1 to 3.

7. A food, a beverage or an oral care preparation comprising the flavor composition for food and drink or for oral care preparations according to claim 6.

8. A food, a beverage or an oral care preparation according to claim 7, wherein said cooling agent, said compound represented by formula (I)

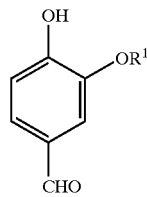

(I)

or said warming agent is present in an amount of 0.000001 to 10% by weight based on the weight of the total composition.

9. A warming composition according to any of claims 1 to 3, wherein said cooling agent is 3-l-menthoxy)-2-methylpropane-1,2-diol.

* * * * *